United States Patent [19]
Fukumoto et al.

[11] Patent Number: 5,292,973
[45] Date of Patent: Mar. 8, 1994

[54] PHOSPHINE OXIDE REMOVAL FROM COMPOUNDS FORMED BY A WITTIG REACTION

[75] Inventors: Takehiko Fukumoto; Akira Yamamoto, both of Niigata, Japan

[73] Assignee: Shin-Etsu Chemical Co., Ltd., Tokyo, Japan

[21] Appl. No.: 81,961

[22] Filed: Jun. 24, 1993

[51] Int. Cl.$^5$ ............ C07C 29/38; C07C 33/025; C07C 17/26; C07C 29/19
[52] U.S. Cl. .................. 568/878; 568/14; 568/909.5; 568/918; 570/189; 570/217; 570/238
[58] Field of Search ............ 568/14, 909.5, 878, 568/918; 570/217, 238, 189

[56] References Cited

U.S. PATENT DOCUMENTS

| | | | |
|---|---|---|---|
| 2,842,599 | 7/1958 | Isler et al. | 570/189 |
| 3,006,939 | 10/1961 | Pommer et al. | 568/878 |
| 3,072,526 | 1/1963 | Butenandt et al. | 568/878 |
| 3,078,256 | 2/1963 | Wittig et al. | 568/14 |
| 3,225,106 | 12/1965 | Rabinowitz | 568/14 |
| 3,361,785 | 1/1968 | McClure | 508/14 |
| 4,206,153 | 6/1980 | Grafen et al. | 568/14 |
| 4,544,779 | 10/1985 | Bright | 568/918 |
| 5,089,659 | 2/1992 | Brueckner et al. | 568/878 |

FOREIGN PATENT DOCUMENTS

| | | | |
|---|---|---|---|
| 241335 | 10/1987 | European Pat. Off. | 570/189 |
| 3426721 | 1/1986 | Fed. Rep. of Germany | 568/14 |
| 962131 | 7/1964 | United Kingdom | 568/909.5 |

*Primary Examiner*—Joseph E. Evans
*Attorney, Agent, or Firm*—Wyatt, Gerber, Burke & Badie

[57] ABSTRACT

An improvement is proposed for the removal of the precipitates of a phosphine oxide compound as a by-product from a mixture thereof with an olefin compound obtained by the Wittig reaction for the preparation of the olefin compound from a phosphorane compound and a carbonyl compound. Instead of the conventional procedure of filtration to remove the precipitates, the mixture in a hydrocarbon solvent, after replacement of a non-hydrocarbon solvent with a hydrocarbon solvent, if necessary, is admixed with a lower carboxylic acid such as acetic acid so that the precipitates of the phosphine oxide are dissolved forming a viscous fluid which is immiscible with the mixture of the olefin compound and the hydrocarbon solvent. The fluid containing the dissolved phosphine oxide compound can be easily removed by phase separation so that a great increase is obtained in the yield of the desired olefin compound.

6 Claims, No Drawings

PHOSPHINE OXIDE REMOVAL FROM COMPOUNDS FORMED BY A WITTIG REACTION

BACKGROUND OF THE INVENTION

The present invention relates to an improvement in the preparation of an olefin compound, more particularly, to an improvement in the step of, in the process for the synthetic preparation of an olefin compound having usefulness as agricultural chemicals, perfumes, biologically active substances and the like by the so-called Wittig reaction for the synthesis of an olefin compound, isolating the olefin compound as the product from the reaction mixture with high efficiency.

As is known, the Wittig reaction is a very efficient route for the synthetic preparation of an olefin compound, in which the carbonyl group in a carbonyl compound is converted specifically and position-selectively into a vinyl group. In a typical procedure utilizing the Wittig reaction, as is described, for example, in Org. React., volume 14, page 270 (1965), an organic phosphonium compound is subjected to a treatment with a basic compound to form a phosphorane compound which is admixed and reacted with a carbonyl compound to give a mixture of an olefin compound and a phosphine oxide compound.

The above mentioned process of the Wittig reaction, however, has a serious problem that, since the reaction mixture after the reaction contains the phosphine oxide compound as a by-product in an equimolar amount to the desired olefin compound, isolation of the desired olefin compound from the reaction mixture is very troublesome. In principle, the olefin compound can be separated from the phosphine oxide compound by filtration. Difficulties are encountered, however, in practicing the filtration process in a large industrial scale because special and expensive facilities are required therefor and pollution of the working environment is more or less unavoidable thereby adverse influences on the workers' health.

A method for facilitating separation of the phosphine oxide compound from the reaction mixture is known, in which the phosphine oxide compound is soluble in an aqueous alkali or acid solution when the phosphine compound of the formula $Ph_2PAr$, in which Ph is a phenyl group and Ar is a group expressed by the formula $C_6H_4COOH$ or $-C_6H_4N(CH_3)_2$, respectively, is used as the starting material in the reaction described in Chem. Ber., volume 99, page 2663 (1966) and J. Chem. Soc., page 2130 (1961) or the so-called Wittig-Horner-Emmons reaction described in Chem. Rev., volume 74, page 87 (1974). This method is advantageous in some respects but several disadvantages are involved therein in that the organic phosphonium salt is a special compound which can be synthesized only by a lengthy synthetic procedure and there may be an adverse influence on the environment due to the alkaline or acidic waste water containing the water-soluble phosphine oxide compound produced in large volumes when the process is practiced in an industrial scale.

On the other hand, it is of course a possible way that the reaction mixture before removal of the phosphine oxide compound is subjected to a procedure of distillation so as to distil out the olefin compound as the desired product by utilizing the difference in the boiling point between the olefin compound and the phosphine oxide compound. A problem in this method is that the boiling point of the reaction mixture under distillation is subject to elevation of boiling point as the distillation proceeds so as to cause troubles due to the stereochemical changes in the molecular structure of the olefin compound, for example, by isomerization or polymerization of the olefin compound caused by the prolonged heating of the reaction mixture as a consequence of the decreased velocity of distillation of the olefin compound. Accordingly, it is eagerly desired to develop a novel and efficient method for the isolation of an olefin compound from the reaction mixture after the Wittig reaction to synthesize the olefin compound.

SUMMARY OF THE INVENTION

The present invention accordingly has an object to provide a novel and improved method for the isolation of an olefin compound from a reaction mixture after the Wittig reaction to synthesize the olefin compound.

Namely, the invention proposes an improvement in the method for the isolation of an olefin compound from a reaction mixture of the olefin compound and a phosphine oxide compound formed by the Wittig reaction of a phosphorane compound and a carbonyl compound, which comprises the steps of:

(a) admixing the mixture in a hydrocarbon solvent with a lower carboxylic acid having 1 to 4 carbon atoms in a molecule to dissolve the phosphine oxide compound forming a fluid containing the same which is immiscible with the mixture of the olefin compound and the hydrocarbon solvent; and (b) separating the fluid containing the phosphine oxide compound from the mixture of the olefin compound and the hydrocarbon solvent.

When the Wittig reaction is conducted in an organic solvent other than hydrocarbons, the reaction mixture after the reaction is first subjected to replacement of the non-hydrocarbon solvent with a hydrocarbon solvent before admixture of the lower carboxylic acid while, when the Wittig reaction is conducted in a hydrocarbon solvent, the reaction mixture as such can be admixed with the lower carboxylic acid.

DETAILED DESCRIPTION OF THE PREFERRED EMBODIMENTS

In the above described inventive method, the phosphine oxide compound precipitated in the reaction mixture, of which the solvent or dispersion medium is a hydrocarbon solvent, obtained by the Wittig reaction of a phosphorane compound and a carbonyl compound is dissolved with a lower carboxylic acid such as acetic acid so that the olefin compound can be taken out of the mixture in the form of a liquid. The olefin compound as the desired product is obtained as a mixture with the hydrocarbon solvent so that the olefin compound can be isolated easily from the mixture by a known method such as distillation.

It is usual in a conventional procedure of the Wittig reaction that a phosphonium salt as the starting material is reacted with a base compound in an organic solvent to form a phosphorane compound either of the stable form or of the non-stable form which is reacted with a carbonyl compound added to the reaction mixture without isolation of the phosphorane compound to give the desired olefin compound as the product.

The base compound is selected depending on the kind of the organic solvent to be combined or depending on the stability of the phosphorane compound formed by the reaction thereof with the phosphonium salt. Examples of the base compound under industrial use in this reaction include potassium tert-butoxide in tetrahydrofuran or in dimethyl sulfoxide, n-butyl lithium in diethyl ether, in hexane or in benzene, sodium hydride in dimethyl formamide, dimsyl sodium or in dimethyl sulfoxide and the like.

The reaction mixture containing the phosphorane compound by the above mentioned reaction is then admixed with a carbonyl compound to effect the Wittig reaction between the carbonyl compound and the phosphorane compound contained in the mixture to give the desired olefin compound as a mixture with the phosphine oxide compound formed as a by-product.

Although the phosphine oxide compound here implied includes triphenyl phosphine oxide, tri(n-butyl) phosphine oxide, tri(n-hexyl) phosphine oxide and the like depending on the kind of the phosphine compound used, it is triphenyl phosphine oxide in most cases because the phosphine compound most frequently used is triphenyl phosphine in respect of the inexpensiveness and good availability.

When the Wittig reaction has come to completion, the reaction is terminated by the addition of water to the reaction mixture. Since it is essential that the reaction mixture is a system of which the solvent or the dispersion medium is a hydrocarbon solvent, the next step is to replace the solvent, assuming that it is a non-hydrocarbon solvent such as diethyl ether, tetrahydrofuran, dimethyl sulfoxide and the like, with a hydrocarbon solvent. Namely, the non-hydrocarbon solvent is removed from the reaction mixture under reduced pressure and the remaining reaction mixture is admixed with a hydrocarbon solvent.

In the selection of the hydrocarbon solvent here used, it is important that the solubility of the phosphine oxide compound therein is as low as possible. It is further important that the hydrocarbon solvent has a boiling point with an as large a difference as possible from that of the olefin compound as the desired product since separation of the hydrocarbon solvent and the olefin compound is undertaken usually by distillation. Examples of the hydrocarbon solvents suitable for this purpose include n-pentane, petroleum ether, isooctane, n-hexane, toluene, benzene, xylene and the like, of which n-hexane, n-pentane, toluene and the like are preferred in view of the inexpensiveness and easiness in handling as well as the low solubility of the phosphine oxide compound therein. The amount of the hydrocarbon solvent is usually in the range from 200 to 600 g per mole of the phosphine oxide compound. Needless to say, when the organic solvent used in conducting the Wittig reaction is a hydrocarbon solvent, the procedure of solvent replacement need not be undertaken.

In the next place, the salt precipitated in the reaction mixture by the reaction of the phosphonium salt and the base compound is dissolved by the admixture of a lower carboxylic acid. The lower carboxylic acid here utilized is a carboxylic acid, preferably, having 1 to 4 carbon atoms in a molecule such as formic acid, acetic acid, propionic acid and butyric acid, of which acetic acid is more preferable. The reaction mixture containing the precipitates is admixed with 30 to 150 g of a lower carboxylic acid or, when the lower carboxylic acid is acetic acid, 50 to 80 g of the acid per mole of the phosphine oxide and the mixture is vigorously agitated at a temperature of, for example, 25° to 30° C. so that the precipitates of the phosphine oxide compound are dissolved by the acid and the reaction mixture is separated into two layers consisting of the upper layer which is a mixture of the hydrocarbon solvent and the olefin compound and the lower layer which is a viscous liquid of the phosphine oxide dissolved in the lower carboxylic acid.

When the above described procedure is undertaken adequately, the viscous liquid phase in the lower layer can contain 95% or more of the phosphine oxide contained in the reaction mixture so that the olefin compound contained in the upper layer can be freed from the phosphine oxide compound almost completely. The viscous fluid containing the phosphine oxide compound is taken by phase separation from the upper layer and is disposed as a waste material by a suitable method such as incineration.

The olefin compound as the desired product contained in the liquid forming the upper layer can be isolated from the mixture by removing the hydrocarbon solvent in a suitable method such as distillation, column chromatography, preparative chromatography, preparative thin-layer chromatography and the like. It is of course desirable in an industrial production of the olefin compound that isolation of the olefin compound from the mixture is conducted by distillation suitable for mass production because the procedure of distillation can be performed without the trouble due to elevation of the boiling point since the mixture subjected to the distillation contains only a very small amount of the phosphine oxide compound in addition to the higher yield of the desired product than the conventional procedure of simple filtration of the reaction mixture after the Wittig reaction.

In the following, the method according to the improvement of the present invention is described in more detail by way of examples and comparative examples which, however, are not construed to limit the scope of the invention in any way.

EXAMPLE 1

The inventive method was applied to the synthetic preparation of Z-11-tetradecen-1-ol as an intermediate in the synthesis of Z-11-tetradecenyl acetate known as a sex pheromone compound of pest insects such as tea tortrix (*Homona magnonima* Diokonoff) and smaller tea tortrix (Adoxophyes sp.).

Thus, 323 g (1 mole) of (trimethylsilyloxyundeca) triphenyl phosphonium bromide and 900 g of tetrahydrofuran were introduced into a reaction vessel to form a mixture which was admixed with 112.2 g (1 mole) of potassium tert-butoxide at a temperature of 15° to 20° C. under an atmosphere of nitrogen and the mixture was agitated for 1 hour at the same temperature. Thereafter, 58 g (1 mole) of propionaldehyde were added dropwise to the mixture by keeping the temperature of the mixture not to exceed −25° C. followed by further continued agitation of the mixture for additional 1 hour at room temperature to complete the reaction.

After completion of the reaction, 15 ml of deionized water were added to the reaction mixture from which tetrahydrofuran was removed under reduced pressure. The reaction mixture was further vigorously agitated with addition of 600 g of n-hexane and 400 g of deionized water. The mixture was separated into two layers by standing and the aqueous phase forming the lower layer was taken and discarded. Thereafter, 80 g of acetic acid were added to the mixture which was again vigorously agitated for 30 minutes. After separation of the mixture into two layers by standing, the viscous fluid in the lower layer was separated and discarded and the liquid in the upper layer, which was a mixture of trimethylsilyloxy Z-11-tetradecene and n-hexane, was admixed with 100 g of a 10% hydrochloric acid and vigorously agitated so that the trimethylsilyl groups were removed to give a solution of Z-11-tetradecen-1-ol in n-hexane. The mixture was separated into two layers by standing and the aqueous phase in the lower layer was discarded. The organic phase in the upper layer, which was a solution of Z-11-tetradecen-1-ol in n-hexane, was washed twice with 300 g of a 2% by weight aqueous solution of sodium hydrogencarbonate and freed from n-hexane under reduced pressure followed by distillation to give 166 g of Z-11-tetradecen-1-ol having a boiling point of 137° to 140° C. under a pressure of 3 mmHg. The yield was 78% of the theoretical value. This product was subjected to the gas chromatographic analysis to determine the geometrical purity to find that the contents of the Z-isomer and the E-isomer were 96% and 4%, respectively.

COMPARATIVE EXAMPLE

Z-11-Tetradecen-1-ol was prepared by the conventional procedure of synthesis involving a step of filtration for the removal of the precipitates of the phosphine oxide after the Wittig reaction.

After completion of the Wittig reaction carried out in substantially the same manner as in Example 1, the reaction mixture was freed from tetrahydrofuran under reduced pressure and then admixed with 500 g of n-hexane with agitation so that triphenyl phosphine oxide was precipitated.

The reaction mixture was freed from the precipitates of triphenyl phosphine oxide by filtration and the filtrate was admixed with 200 g of a 10% hydrochloric acid to remove the trimethylsilyl groups from the trimethylsilyloxy Z-11-tetradecene. The mixture was freed from n-hexane under reduced pressure and subjected to distillation to give 144 g of Z-11-tetradecen-1-ol. The yield was 68% of the theoretical value.

EXAMPLE 2

The inventive method was applied to the synthetic preparation of 1-chloro-E,Z-7,9-dodecadiene as an intermediate in the synthesis of E,Z-7,9-dodecadienyl acetate known as the sex pheromone of European grapevine moth (*Lobesia botrana*).

Thus, 270 g of n-propyl triphenyl phosphonium bromide and 600 ml of tetrahydrofuran were introduced into a reaction vessel to form a mixture, into which 76 g of potassium tert-butoxide were added at a temperature of 15° to 20° C. under an atmosphere of nitrogen and the mixture was agitated for 30 minutes. Thereafter, 122 g of 9-chloro-E-2-nonenal were added dropwise to the mixture at the same temperature as above and agitation of the mixture was continued for further 1 hour to complete the reaction.

The reaction mixture after completion of the reaction was freed from tetrahydrofuran under reduced pressure and then admixed with 150 g of deionized water and 300 g of n-hexane followed by vigorous agitation. The reaction mixture was kept standing to be separated into two layers, of which the aqueous phase in the lower layer was discarded. The organic phase in the upper layer was admixed with 40 g of acetic acid and vigorously agitated for 30 minutes followed by standing to be separated into two layers. The viscous fluid in the lower layer was discarded and the liquid in the upper layer was washed with a 2% by weight aqueous solution of sodium hydrogencarbonate followed by removal of n-hexane under reduced pressure. The remaining liquid was subjected to distillation under reduced pressure to give 119 g of 1-chloro-E,Z-7,9-dodecadiene having a boiling point of 126° to 127° C. under a pressure of 4 mmHg. The yield was 84.9% of the theoretical value. This product was subjected to the gas chromatographic analysis for the determination of the geometrical purity to find that the contents of the E,Z-isomer and the E,E-isomer were 89% and 11%, respectively.

What is claimed is:

1. In a method for the removal of a phosphine oxide compound from a mixture of the phosphine oxide compound and an olefin compound formed by a Wittig reaction for the preparation of the olefin compound from a phosphorane compound and a carbonyl compound, the improvement which comprises the steps of:
    (a) admixing the mixture in a hydrocarbon solvent with a lower carboxylic acid having 1 to 4 carbon atoms in a molecule to dissolve the phosphine oxide compound forming a fluid containing the phosphine oxide compound which is immiscible with the mixture of the olefin compound and the hydrocarbon solvent; and
    (b) separating the fluid containing the phosphine oxide compound from the mixture of the olefin compound and the hydrocarbon solvent.

2. The improvement according to claim 1 in which the hydrocarbon solvent is selected from the group consisting of n-pentane, petroleum ether, isooctane, n-hexane, benzene, toluene and xylene.

3. The improvement according to claim 1 in which the lower carboxylic acid is acetic acid.

4. The improvement according to claim 1 in which the amount of the hydrocarbon solvent is in the range from 200 g to 600 g per mole of the phosphine oxide compound.

5. The improvement according to claim 1 in which the amount of the lower carboxylic acid is in the range from 30 g to 150 g per mole of the phosphine oxide compound.

6. In a method for the removal of precipitates of a phosphine oxide compound from a mixture of the phosphine oxide compound and an olefin compound in a non-hydrocarbon solvent formed by a Wittig reaction for the preparation of the olefin compound from a phosphorane compound and a carbonyl compound, the improvement which comprises the steps of:
    (a1) removing the non-hydrocarbon solvent from the mixture;
    (b1) admixing the mixture after removal of the non-hydrocarbon solvent with a hydrocarbon solvent;
    (c1) admixing the mixture after admixture of the hydrocarbon solvent with a lower carboxylic acid having 1 to 4 carbon atoms in a molecule to dissolve the precipitates of the phosphine oxide compound forming a fluid containing the phosphine oxide compound which is immiscible with the mixture of the olefin compound and the hydrocarbon solvent; and
    (d1) separating the fluid containing the phosphine oxide compound from the mixture of the olefin compound and the hydrocarbon solvent.

* * * * *